US009302846B2

(12) United States Patent
Bell et al.

(10) Patent No.: US 9,302,846 B2
(45) Date of Patent: Apr. 5, 2016

(54) SELF-CONTAINED DEVICES FOR TREATING MEDICAL WASTE AND METHODS IF THEIR USE

(71) Applicants: Jeffrey Bell, Sudbury, MA (US); Andre Philippe Nault, East Longmeadow, MA (US); Robert Todd Winkowicz, North Andover, MA (US); Peter Bates, Framingham, MA (US); Benjamin Hall, Boston, MA (US)

(72) Inventors: Jeffrey Bell, Sudbury, MA (US); Andre Philippe Nault, East Longmeadow, MA (US); Robert Todd Winkowicz, North Andover, MA (US); Peter Bates, Framingham, MA (US); Benjamin Hall, Boston, MA (US)

(73) Assignee: STERILIS MEDICAL CORPORATION, Boxborough, MA (US)

( * ) Notice: Subject to any disclaimer, the term of this patent is extended or adjusted under 35 U.S.C. 154(b) by 513 days.

(21) Appl. No.: 13/746,977

(22) Filed: Jan. 22, 2013

(65) Prior Publication Data

US 2014/0202116 A1 Jul. 24, 2014

(51) Int. Cl.

*B65F 1/06* (2006.01)
*A61L 11/00* (2006.01)
*B65F 1/14* (2006.01)

(52) U.S. Cl.

CPC ................. *B65F 1/06* (2013.01); *B65F 1/1473* (2013.01); *B65F 1/1615* (2013.01); *B65F 2210/138* (2013.01); *B65F 2210/162* (2013.01); *B65F 2210/167* (2013.01); *B65F 2210/168* (2013.01); *B65F 2210/188* (2013.01); *B65F 2240/145* (2013.01)

(58) Field of Classification Search

CPC ......... A61L 11/00; A61L 2/00; A61L 2/0094; A61L 2/20; B65F 1/1468
USPC ............. 53/121, 523, 529, 512, 127; 422/308
See application file for complete search history.

(56) References Cited

U.S. PATENT DOCUMENTS 5,130,092 A * 7/1992 Liu ................................ 422/28
5,340,536 A 8/1994 Datar et al.
5,348,235 A 9/1994 Pappas
5,364,589 A 11/1994 Buehler et al.
5,550,311 A 8/1996 Young
5,570,845 A 11/1996 Lewis et al.
5,611,947 A 3/1997 Vavruska
5,614,157 A 3/1997 Hall
5,720,438 A 2/1998 Devine et al.
5,870,885 A * 2/1999 Biddle et al. .................... 53/436
6,113,854 A 9/2000 Micum et al.
6,141,945 A * 11/2000 Becher ............................ 53/527
6,446,887 B1 9/2002 Swisher et al.
6,732,962 B1 5/2004 Butler
7,144,550 B2 12/2006 Devine et al.

(Continued)

FOREIGN PATENT DOCUMENTS

WO WO97/26019 A1 7/1997
WO WO2004/062825 A2 7/2004

(Continued)

*Primary Examiner* — Gloria R Weeks
(74) *Attorney, Agent, or Firm* — James G. Shelnut; Jeda Patentry

(57) ABSTRACT

Disclosed and claimed herein are devices for the treatment of medical waste using high temperature and pressure steam. The devices are designed to be self-contained and are movable by one person of average strength and ability. The devices are self-contained and require no special installation, connections, plumbing or permanent or semi-permanent electrical connections. Disclosed and claimed herein are methods using the disclosed and claimed devices.

20 Claims, 2 Drawing Sheets

(56) References Cited

U.S. PATENT DOCUMENTS

| | | | |
|---|---|---|---|
| 7,195,743 | B2 | 3/2007 | Butler |
| 7,347,391 | B2 | 3/2008 | Michalek et al. |
| 7,815,851 | B1 | 10/2010 | Lewis |
| 7,931,860 | B1 | 4/2011 | Lewis et al. |
| 8,128,888 | B2 | 3/2012 | Bacik et al. |
| 8,153,078 | B2 | 4/2012 | Bacik et al. |
| 8,282,892 | B2 | 10/2012 | Sampson |
| 2003/0147771 | A1 | 8/2003 | Hodgins |
| 2006/0255191 | A1 | 11/2006 | Chiang et al. |
| 2008/0217444 | A1 | 9/2008 | Michalek et al. |
| 2010/0135851 | A1 | 6/2010 | Michalek et al. |
| 2011/0165035 | A1 | 7/2011 | Lewis et al. |
| 2013/0175373 | A1 | 7/2013 | Morgan et al. |
| 2013/0287628 | A1 | 10/2013 | Smith et al. |
| 2013/0306763 | A1 | 11/2013 | Carmel |

FOREIGN PATENT DOCUMENTS

| | | | |
|---|---|---|---|
| WO | WO2011/079853 | A1 | 7/2011 |
| WO | WO2013/075162 | A1 | 5/2013 |

* cited by examiner

SELF-CONTAINED DEVICES FOR TREATING MEDICAL WASTE AND METHODS IF THEIR USE

FIELD OF THE INVENTION

The present disclosure is in the field of the treatment of medical waste, and more particularly in the field of self-contained devices and methods for treating medical waste.

BACKGROUND OF THE INVENTION

Current devices and methods for treating medical waste include collecting the waste, storing the waste for a period of time, transporting the waste to a waste treatment center and disposing of the waste by such methods as incineration. The waste can be stored for up to 1 year and amounts of the waste can exceed 1 ton. As a result, medical waste festers during storage and is extremely dangerous to handle when collecting, transporting and disposing of the waste. In addition, the movement of medical waste from its point of origin to a storage area exposes handlers, facilities and the environment to potential contamination.

In response to these issues, devices and methods have been described that treat medical waste at the facility in which it is created. The waste is collected and, in some cases stored prior to being placed in the device and essentially sterilized using a number of techniques, either individually or collectively, including chemical treatment, steam autoclaving and disinfecting. The now treated waste is then collected, packaged, transported and discarded, as the waste is no longer considered, by law, a biological hazard. These devices are generally large, expensive, permanent fixtures which still require collection of the medical waste from the point of origin by personnel which may not be fully trained in the science of infectious waste exposure or emergency procedures needed in the case of a spill or other accident. The operation and maintenance of these devices also require extensive training.

In response to these issues, devices and methods have been described which are smaller and more suitable for being present on hospital floors, in emergency rooms, or in treatment rooms, places where medical waste is generated. Medical waste is collected in red bags, or in sharps containers, until sufficiently full and then transferred to a treatment area treated to render the waste biologically benign. These devices however generally need special plumbing, and special electrical power connections. Once installed these devices are generally intended to remain stationary and are very work intensive to move from one area of need to another area of need, such as within a clinic, on a hospital floor, or between hospital rooms where items like bandages, gloves, sharps paper towels and the like need to be disposed of quickly before any possibly contaminating materials can be spread. Thus there is an ongoing, unmet need for devices and methods for the treatment of medical waste at the point of origin that is sized to fit readily within a medical environment and be readily moved by one person of ordinary strength and ability and be self-contained such that no special assembly or disassembly is required for the device to be moved.

SUMMARY OF THE DISCLOSURE

The present disclosure relates to novel self-contained devices for treating medica waste at the point of care, and methods of their use.

In a first embodiment, disclosed and claimed herein is a self-contained medical waste sterilization and processing device comprising a housing comprising at least one ingress connected to a first sealable compartment capable of receiving steam and maintaining elevated steam pressure, a steam generating component connected to the first sealable compartment for supplying steam at elevated pressures to the compartment, a grinder situated after the first compartment and a second compartment configured to receive steam-treated medical waste from the first compartment, to package the waste and to seal the package containing the waste for removal from an egress in the housing, and a water reclamation system configured to remove excessive moisture from the first sealable compartment and return it to the steam generating component wherein the steam generating component is self-contained and free of external connections to a water supply, and wherein the package is optionally vacuum heat sealed.

In a second embodiment, disclosed and claimed herein is a self-contained medical waste sterilization and processing device of the above embodiment wherein the steam generating component comprises a steam generator and a water reservoir, wherein the water reservoir is configured to supply water to the steam generator and receive water from the water reclamation system.

In a third embodiment, disclosed and claimed herein are the self-contained medical waste sterilization and processing device of the above embodiments wherein the devices operate using standard electrical power as supplied by a wall outlet.

In a fourth embodiment, disclosed and claimed herein are the self-contained medical waste sterilization and processing devices of the above embodiments wherein the devices are free of attachments requiring installation.

In a fifth embodiment, disclosed and claimed herein is a self-contained medical waste sterilization and processing device of the above embodiments further containing at least one RFID identification and tracking device provided with the package and/or a radiation detection system.

In a sixth embodiment, disclosed and claimed herein is a self-contained medical waste sterilization and processing device of the above embodiments further configured to be portable and movable by a person of ordinary strength and ability without the use of mechanical assistance.

In a seventh embodiment, disclosed and claimed herein is a self-contained medical waste sterilization and processing device of the above embodiments further containing at least one programmable logic system into which is logged proper medical waste treatment parameters for the device based on regional requirements and optionally a programmable logic system for analyzing the time of treatment, the steam temperature and the steam pressure for treatment of the medical waste and relaying the data to device controls and log files.

In an eighth embodiment, disclosed and claimed herein is a self-contained medical waste sterilization and processing device of the above embodiments, further containing a quality control system for calibration and performing analysis of the components, compartments and systems of the devices In a ninth embodiment, disclosed and claimed herein is a self-contained medical waste sterilization and processing device of the above embodiments, further comprising a self-cleansing system for routine maintenance and cleaning of the first compartment.

In a tenth embodiment, disclosed and claimed herein are methods of treating medical waste containing the steps of obtaining the device of any of the above embodiments, introducing the medical waste to the first sealable compartment via the ingress, treating the medical waste by exposing the waste to high temperature steam and pressure from the boiler, removing a substantial amount of moisture from the treated waste, capturing the moisture by condensing it and routing it back to the steam generating component, grinding and shredding the treated waste, moving the treated waste to a heat sealable bag in the second compartment, providing a unique identifier to the bag, optionally substantially removing air from the bag, sealing the bag, and removing the sealed bag from the device.

DETAILED DESCRIPTION OF THE DISCLOSURE

Figure 1:
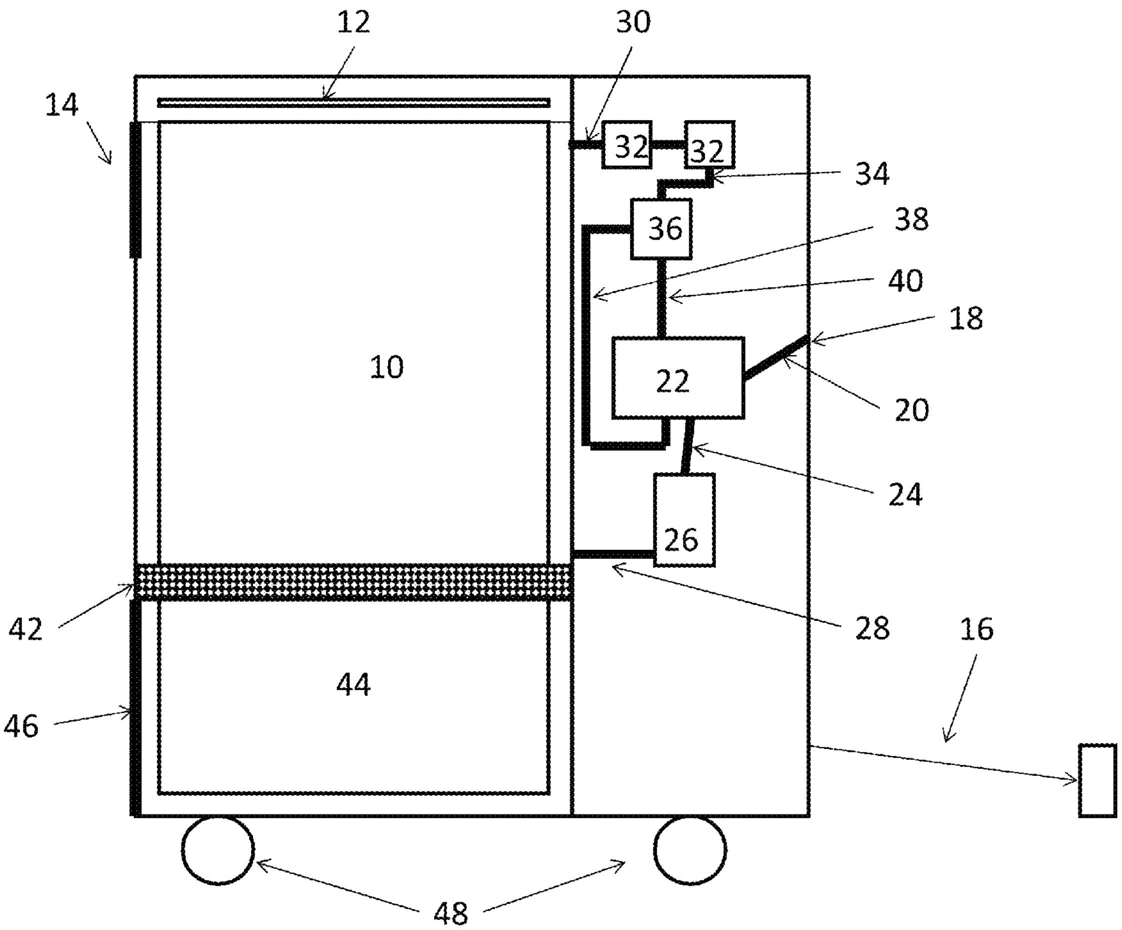
FIG. 1 shows a graphic description of one embodiment device for treatment of medical waste as disclosed and claimed herein.

As used herein, the conjunction "and" is intended to be inclusive and the conjunction "or" is not intended to be exclusive unless otherwise indicated. For example, the phrase "or alternatively" is intended to be exclusive.

As used herein the term sterilization refers to the process of eliminating, or reducing to an acceptable level, infectious materials such as germs, noxious materials, bacteria, viruses and the like, or potentially infectious materials such as blood and other bodily fluids, rendering them harmless.

As used herein the term "installation" refers to permanent or semi-permanent fixtures which require placing devices into position and connecting. The term does not refer to simple plug and unplug of an electrical cord into a standard and readily obtainable electrical outlet.

The current disclosure is intended for all medical waste which is requires sterilization to be rendered harmless, including human and animal waste as well as other biological materials found in laboratories or area where work on biologically active materials occurs.

As used herein the terms "grinder", "shredder", "grinding" and "shredding" refer to devices and processes that transform the medical waste into an unrecognizable form through the actions of cutting, slicing, chopping, pulverizing and the like.

Disclosed and claimed herein is a self-contained medical waste sterilization and processing device having a housing made from any structural material such as high impact plastic such as high impact polystyrene, or metals such as any of a number of stainless steel types or aluminum. The housing materials are readily cleanable and do not support the growth or survival of the materials to be sterilized.

The housing is fitted with an ingress allowing materials for treatment to be placed into the device. The ingress may be a sliding door, a lid, or other covered opening and may be provided with a lock, a logging device to measure when materials have been added to the device, or other mechanism to secure the ingress. The ingress may be situated on the top, the side or other area on the device to provide for convenient operation.

The device contains a first sealable compartment connected to the ingress such that waste materials to be treated are placed in the first compartment. The compartment may be constructed of any structural material that can withstand the operational temperatures and pressures of the device. When the waste is input, a lid closes and is secured and the first compartment is sealed using typical components of gaskets, locks and devices well known in the art, so that when high temperature steam is introduced it is contained within the compartment during the sterilization operation. The compartment is also fitted with sensors to determine time, temperature, and duration of the sterilization processes, which may interface with a programmable logic system.

A self-contained steam generator component is contained in or on the housing and is configured to provide steam to the first sealable compartment during operation. The steam generating component contains a steam generator including, for example, a boiler system, a heat exchanger and the like that is heated by electrical power supplied from a standard wall outlet and the steam that is generated is conducted to the first sealable compartment. The steam may be conducted directly to the first sealable compartment or it may first be directed to a high pressure steam reservoir wherein the steam is then directed to the first sealable compartment. The steam conduits may be fabricated from metal, rubber, plastic and the like. The self-contained steam generator component also contains a water reservoir configured to supply water to the steam generator and receive water from the water reclamation system. Due to the nature of the disclosed self-contained devices there are no pipes or other connections to an external water supply that feeds the steam generating component, such pipes and connections requiring installation and deinstallation when portability is desired. This undesirable need for installation and deinstallation allows for increased freedom of mobility of the disclosed device not available in other waste treatment devices. The water reservoir may be filled periodically by opening an inlet into the reservoir and filling it to a desired level, determined by the amount of medical waste processed, the efficiency of recycling the excessive water from the treated material and the acceptable amount of water contained in the packaged material.

The water reclamation system is positioned between the first sealable compartment and the water reservoir. It is configured to substantially remove excess moisture from the treated waste in the first sealable compartment prior to further processing. The first compartment may be heated using electric power to evaporate the excess moisture, the moisture being conducted to a condenser for collection and return to the boiler. Fans and vacuum may be used to help evacuate moisture from the compartment and/or direct it to water reclamation components such as, for example, condensers cooled by water directed from and returned to the water reservoir. The water reclamation system further may contain purification components such as, for example, HEPA filter, activated carbon filters and the like, situated prior to the water entering the water reservoir. As added precautions, other components may be present to ensure that water returning to the boiler is highly purified, such as, for example, treatment with UVC light radiation and/or ozone.

In this way the steam generating component continually is supplied with water for making steam. The temperature of the steam for sterilization of medical waste is between about 110° C. to about 150° C. and the pressure is between about 15 to about 60 psi. Depending on the amount of waste to be treated and the local legal requirements, the time of treatment may run from at least about 2 minutes to over an hour.

The device may also include a compactor for reducing the volume of the waste situated in the first sealable compartment. The compactor may be driven by a piston, a hinged plate or other compacting device driven by pneumatics, hydraulics or other forms of force.

Situated after the first sealable compartment is a grinder for grinding and shredding the sterilized medical waste into small pieces rending them unrecognizable as desired. Grinders and shredders suitable for devices of the current disclosure include those well known in the art for grinding medical waste into an unrecognizable form, such as, for example, those disclosed in U.S. Pat. No. 7,195,743 to Butler, incorporated herein by reference, limited to what is disclosed for grinding and shredding of medical waste.

The device of the current disclosure also contains a second compartment which receives the treated waste from the first compartment. The treated waste may be moved to the second compartment by a number of methods including gravity feed, a piston or a flap that lifts up and moves the waste along.

The second compartment is further configured to package the treated waste. There is provided a bagging system which accepts the treated waste when moved from the first compartment. The bags are designed to withstand any heat processes, such as, for example, high density polyethylene, polypropylene or other polyolefin, polystyrene, PET, and the like. When the waste is placed in the bag, the bag may be heat sealed. Substantially all the air may be removed from the bag using a vacuum pump prior to sealing the bag. The bags may contain RFID tags which allow for unique identification of the bag with any number of desired information including, for example the waste producer, the amount of the waste, the levels of treatment, the point of origin, waste types, and the like. The bags may alternatively contain other indicia designed to uniquely identify the bag. The tags may be inherent to the bag or may be added to the bag during processing depending on the desired information needed on the tag. The packaged waste can be removed from an egress positioned in the front, side or back of the device as desired.

The devices of the current disclosure run on standard electrical power as obtained from a standard wall outlet. For example, in North America, northern South America and Japan, standard electric power is typically supplied at 100-127 V, 50-60 Hz to a wall socket. Most of the rest of the world supplies standard electrical power at 200-240 V, 50-60 Hz to their wall outlets. The current devices use a typical standard plug and wire that plugs into the wall and is readily removed. Thus, no special wiring designs or permanent or semi-permanent installation are required.

Some regulations require either longer treatment times or higher temperatures of steam when steam treating the waste, or both. To provide proper treatment the devices of the current disclosure are provided with at least one programmable logic system which into required parameters may be entered, including, for example, steam temperature, steam pressure, time of exposure of the medical waste to the steam, grinding/shredding parameters, unique identifiers of the waste, including the point of origin. The programmable logic system may relay the information of the process and other unique identifiers to output devices such as, for example, RFID tags, bar codes, alpha-numeric indicia, or other identifying indicia.

A radiation detection device may also be included in the device. Many waste treatment regulations require that radioactive waste be treated differently from other medical waste, for example, medical waste treated to the level of local requirements may be disposed in a land fill, while waste containing any radioactive waste is barred from such disposal. Thus the device can be used to prevent radioactive waste from being mixed with "regular" medical waste.

In other certain embodiment of the disclosed devices, the device is configured for mobility. As mentioned, the devices are self-contained and free of external connections. The power supplied to the devices is through a standard plug into a standard wall outlet. Wheeling components such as wheels, castors and the like are positioned on the bottom of the device so that the device can be moved from room to room or area to area as desired. The wheeling components may include braking levers which prevent the components from moving until the levers are flipped back freeing the components to allow device movement. The devices in these embodiments are designed so that only one person, of average strength and ability, can move the device. Thus the device is below a weight and dimension that allows the movement of the device by one average person.

The devices of the current disclosure may also include quality control systems which check to calibrate the device and ensure that the various components, compartments and system of the device is in the proper operating condition such that, in operation, the device will provide the required sterilization of the medical waste. The programmable logic device can signal the various components, compartments and systems to provide feedback for operation. The logic device can then signal the operator that the device is working properly or if and where in the device a problem exists.

Methods of treating medical waste using the devices disclosed in any of the above embodiments are disclosed and claimed herein, including the steps of introducing medical waste into the first sealable compartment of the device via an ingress, treating the medical waste by exposing the waste to high temperature steam and pressure from the self-contained steam generating component for a desired length of time with steam at a desired temperature and pressure, the parameters of which may have been preprogrammed into the device using at least one programmable logic system, removing a substantial amount of moisture from the treated waste, capturing the moisture by condensing it and routing it back to the steam generating component, optionally compacting the waste. A second treatment of the medical waste is then applied using the same or different parameters are desired. The treated medical waste is then conducted through a grinder/shredder and into the second compartment. The second compartment is fitted with a heat sealable bag. The air may then be optionally substantially removed from the bag, the bag sealed, and removed from the device. The bag may be tracked using an RFID tag or other indicia and may be deposited in a land fill.

The disclosed methods may include programming the required operational parameters into the device using a programmable logic system. These methods may also include a cleansing step after the treatment of medical waste has occurred wherein the first sealable compartment is treated with high temperature steam taken from the steam generating component. The method may also include a quality control step wherein the logic system performs a series of checks to ensure the device is operating properly compared to the programmed parameters.

When the device needs to be moved, the electrical cord is removed from the wall and a person wheels the device to another area and plugs the electrical cord back into an outlet in the other area.

Figure 2:
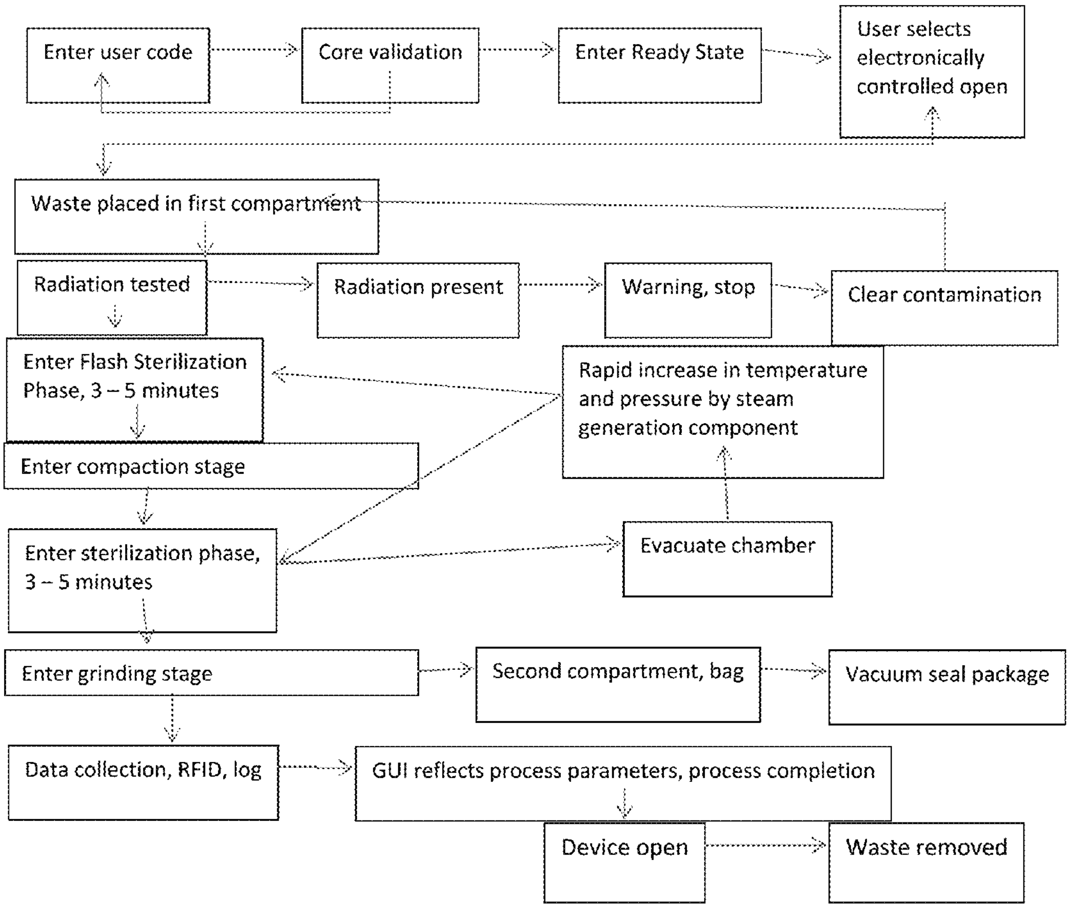
FIG. 2 shows a flow chart of one embodiment method disclosed and claimed herein.

Referring to the figures, FIG. 1 depicts a graphic representation of one embodiment of the disclosure. The device contains a first sealable compartment 10, optionally containing a compaction component 12. An inlet 14 allows medical waste to be introduced into the compartment 10. The device runs on electricity obtained from a standard electrical wall socket using a standard electrical cord 16. A water reservoir 22, having a water inlet 18 for supplying water through conduit 20 as need, is connected to a steam generator 26 through conduit 24. Steam is injected into the compartment 10 through conduit 28. The steam may first be contained in a steam reservoir (not shown) prior to entering compartment 10. Excess steam or water may be returned to the steam generating component by passing through conduit 30 into cleaning mechanisms 32 then through conduit 34 into a condenser 36 to be collected in the water reservoir 22 through conduit 40. Conduit 38 is provided to supply the condenser with cooling water for converting any remaining steam into water. A grinding/shredding device 42 is provided between the first compartment 10 and the second compartment 44. After waste is collected in a bag, sealed, and identified, the bag is removed through egress 46. The device is portable and movable using medical graded castors 48. Referring to FIG. 2, one method of the current disclosure is illustrated.

Although the present invention has been shown and described with reference to particular examples, various changes and modifications which are obvious to persons skilled in the art to which the invention pertains are deemed to lie within the spirit, scope and contemplation of the subject matter set forth in the claims.

We claim:

1. A self-contained medical waste sterilization and processing device comprising a housing comprising:

a. at least one ingress connected to a first sealable compartment, optionally comprising a compaction device, capable of receiving steam and maintaining elevated steam pressure, b. a steam generating component connected to the first sealable compartment for supplying steam at elevated pressures to the compartment, c. a grinder component situated after the first compartment, d. a second compartment configured to receive steam-treated medical waste from the first compartment, to package the waste and to seal the package containing the waste for removal from an egress in the housing, and e. a water reclamation component configured to remove excessive water from the first sealable compartment and return it to the steam generating component, wherein the steam generating component is self-contained and free of external connections to a water supply, and wherein the package is optionally vacuum heat sealed.

2. The device of claim 1, wherein the steam generating component comprises a steam generator and a water reservoir, and optionally a steam reservoir, wherein the water reservoir is configured to supply water to the steam generator and receive water from the water reclamation component.

3. The device of claim 2, wherein the device operates using standard electrical power as supplied by a wall outlet.

4. The device of claim 2, wherein the device is free of attachments requiring installation.

5. The device of claim 4, wherein the device is portable.

6. The device of claim 5, further comprising a programmable logic system for user identification and analyzing the time of treatment, the steam temperature and the steam pressure for treatment of the medical waste and relaying the data to device controls and log files.

7. The device of claim 6, further comprising at least one RFID identification, bar code, or identifying indicia or tracking device provided with the package.

8. The device of claim 7, further comprising a radiation detection system.

9. The device of claim 8, further comprising a system for cleansing the first sealable compartment.

10. The device of claim 8, further comprising a quality control system interfaced with the programmable logic system to ensure proper operating parameters.

11. A method of treating medical waste comprising the steps of obtaining the device of claim 1, and a. introducing the medical waste to the first sealable compartment via the inlet, b. treating the medical waste by exposing the waste to high temperature steam and pressure from the steam generating component at least about 3 minutes, c. optionally compacting the waste, d. treating the medical waste by exposing the waste to high temperature steam and pressure from the steam generating component a second time for at least about 3 minutes, e. removing a substantial amount of moisture from the treated waste and returning it to the steam generation system, f. grinding or shredding the treated waste, g. moving the treated waste to a heat sealable bag in a the second compartment, h. optionally substantially removing air from the bag, i. sealing the bag, and j. removing the sealed bag from the device.

12. The method of claim 11, wherein the steam generating component comprises a steam generator and a water reservoir, and optionally a steam reservoir, wherein the water reservoir is configured to supply water to the steam generator and receive water from the water reclamation component.

13. The method of claim 12, wherein the device operates using standard electrical power as supplied by a wall outlet.

14. The method of claim 13, wherein the device is free of attachments requiring installation.

15. The method of claim 14, wherein the device is portable.

16. The method of claim 15, wherein the device further comprising a programmable logic system for user identification and analyzing the time of treatment, the steam temperature and the steam pressure for treatment of the medical waste and relaying the data to device controls and log files and the method further comprises the steps of entering a user code, analyzing the time of treatment, the steam temperature and the steam pressure for treatment of the medical waste and relaying the data to device controls and log files.

17. The method of claim 16, wherein the programmable logic system provides identification for the sealed bag, RFID tags, bar codes, or indicia.

18. The method of claim 15, wherein the device further comprises a radiation detection system and the method further comprises the step of determining radiation in the medical waste prior to sterilization.

19. The method of claim 15, further comprising the step of cleansing the first sealable compartment after the treated waste is removed.

20. The method of claim 15, wherein the device further comprises a quality control system interfaced with the programmable logic system to ensure proper operating parameters.

* * * * *